United States Patent [19]

Hamlin

[11] Patent Number: 5,270,086
[45] Date of Patent: Dec. 14, 1993

[54] MULTILAYER EXTRUSION OF ANGIOPLASTY BALLOONS

[75] Inventor: Robert N. Hamlin, Stillwater, Minn.

[73] Assignee: Schneider (USA) Inc., Plymouth, Minn.

[21] Appl. No.: 727,664

[22] Filed: Jul. 9, 1991

Related U.S. Application Data

[63] Continuation-in-part of Ser. No. 411,649, Sep. 25, 1989, abandoned.

[51] Int. Cl.[5] ............................................. A61M 29/02
[52] U.S. Cl. ................................... 428/35.2; 428/36.9; 428/36.92; 606/192; 604/96
[58] Field of Search .............. 606/192, 194; 604/96; 428/34.9, 35.2, 36.9, 36.92, 35.7

[56] References Cited

U.S. PATENT DOCUMENTS

| | | | |
|---|---|---|---|
| 3,861,972 | 1/1975 | Glover et al. | 156/86 |
| 4,211,741 | 7/1980 | Ostoich | 264/173 |
| 4,265,848 | 5/1981 | Rüsch | 264/130 |
| 4,318,947 | 3/1982 | Joung | 528/399 |
| 4,351,341 | 9/1982 | Goldberg et al. | 128/348 |
| 4,413,989 | 11/1983 | Schjeldahl et al. | 604/96 |
| 4,444,188 | 4/1984 | Bazell et al. | 128/348.1 |
| 4,490,421 | 12/1984 | Levy | 428/36.9 |
| 4,627,844 | 12/1986 | Schmitt | 604/264 |
| 4,684,363 | 8/1987 | Ari et al. | 606/192 |
| 4,729,914 | 3/1988 | Kliment et al. | 428/35.7 |
| 4,744,366 | 5/1988 | Jang | 606/192 |
| 4,775,371 | 10/1988 | Mueller, Jr. | 604/280 |
| 4,803,035 | 2/1989 | Kresge et al. | 264/519 |
| 4,810,543 | 3/1989 | Gould et al. | 428/35.7 |
| 4,824,618 | 4/1989 | Strum et al. | 264/37 |
| 4,932,956 | 6/1990 | Reddy et al. | 606/192 |
| 4,932,958 | 6/1990 | Reddy et al. | 606/192 |
| 4,952,357 | 8/1990 | Euteneuer | 604/96 |
| 5,035,694 | 7/1991 | Kasprzyk | 606/192 |

Primary Examiner—Ellis P. Robinson
Assistant Examiner—Rena L. Dye
Attorney, Agent, or Firm—Haugen and Nikolai

[57] ABSTRACT

A method of producing laminated inflatable, substantially inextensible expander members having composite properties enhancing their use on intravascular catheters, such as angioplasty catheters is described. Diverse polymeric compounds of differing properties are coextruded to create a multilayer parison. The parison is subsequently drawn and expanded in a blow molding operation to yield an expander member exhibiting enhanced properties including lubricity, burst-strength, limited radial expansion, bondability, and rupture characteristics.

18 Claims, 3 Drawing Sheets

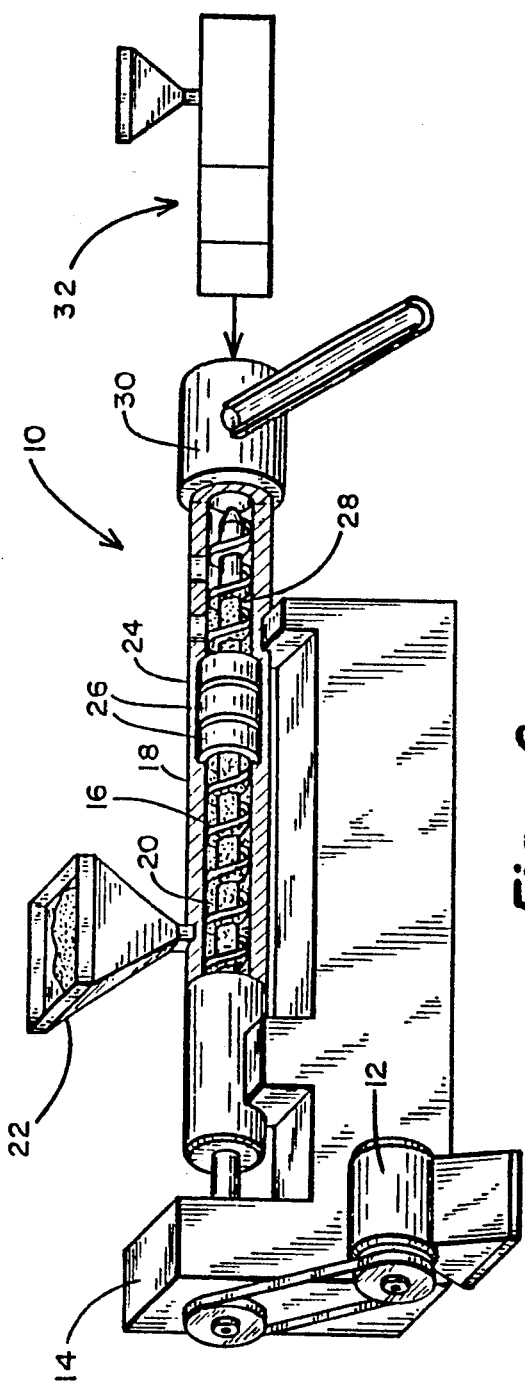
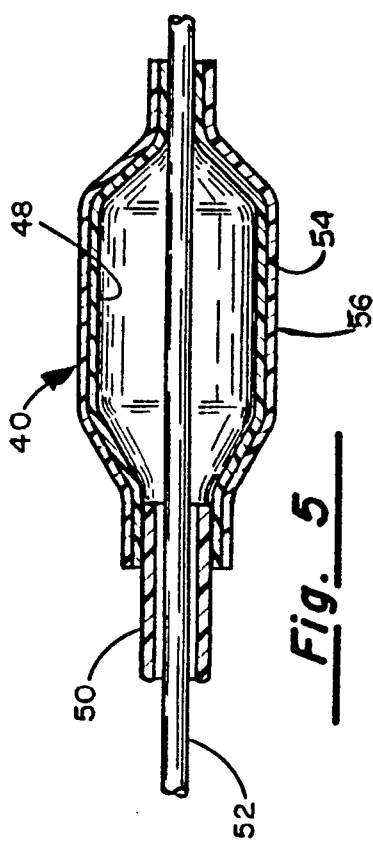

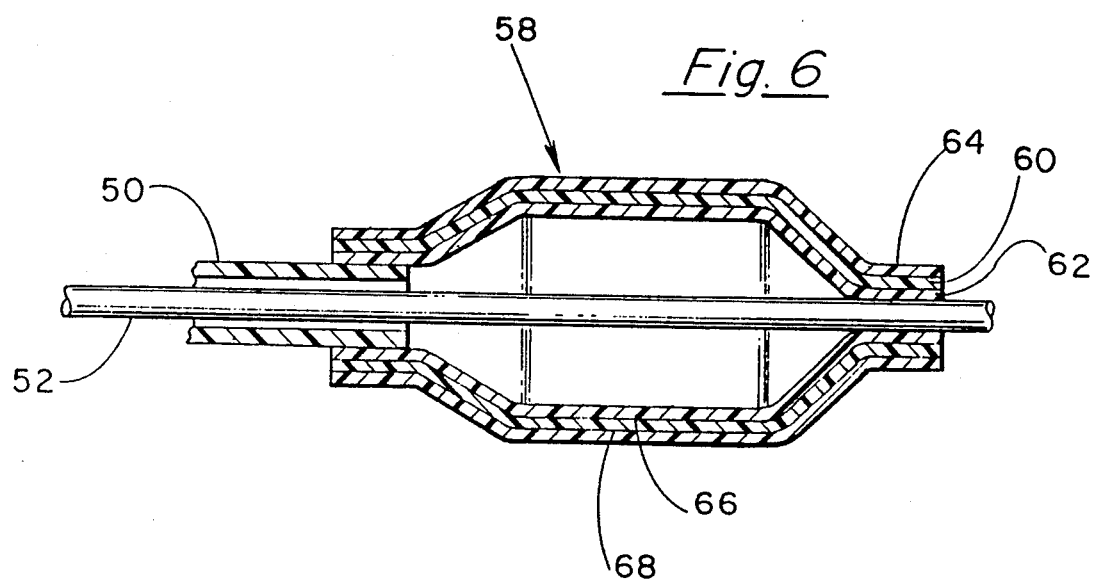

MULTILAYER EXTRUSION OF ANGIOPLASTY BALLOONS

This application is a continuation-in-part of application, Ser. No. 07/411,649, filed on Sep. 25, 1989, which is now abandoned.

BACKGROUND OF THE INVENTION

I. Field of the Invention

This invention relates generally to balloon catheters, and more particularly to a method for fabricating a multilayer balloon composite exhibiting enhanced characteristics attributable to the properties of the individual layers.

II. Discussion of the Prior Art

As an alternative to open-heart, coronary bypass surgery, a technique referred to coronary transluminal angioplasty has been developed following the pioneering introduction of the technique by A. Gruntzig. In carrying out this procedure, a dilatation catheter having an inflatable expander member (balloon) on the distal end thereof is routed through the vascular system to a location within a coronary artery containing a stenotic lesion. Following placement of the expander member across the lesion, a fluid is introduced into the proximal end of the catheter and is used to inflate the expander member to a predetermined relatively high pressure whereby the lesion is compressed into the vessel wall restoring patency to the previously occluded vessel.

It is desirable that the composite expander member exhibit the following characteristics:

1. High burst (tensile) strength;
2. Low radial expansion at elevated pressures;
3. Ease of bonding to a catheter body;
4. Failure characteristics avoiding pinhole ruptures; and
5. Low coefficient of friction.

The Schjeldahl et al. U.S. Pat. No. 4,413,989 owned by applicants' assignee discloses a coronary transluminal angioplasty catheter in which the expander member is formed from polyethylene terephthalate in a drawing and blow molding process so as to provide biaxial orientation to the material. Such PET balloons are found to exhibit the desirable property of high burst strength and relatively low radial expansion when inflated to seven atmospheres or more. However, because the catheter body itself is generally fabricated from a formulation containing silicon rubber, polyethylene, PET or polyurethane, a problem exists when attempts are made to bond the expander member to the distal end portion of the catheter body. The PET polyester balloon tends not to adhere easily to the catheter body especially in a thermal bonding process.

Moreover, experience with polyethylene, PVC and polypropylene expansion members has shown that at relatively high pressures, pinhole leaks form which may create a high velocity jet of inflation fluid capable of perforating the blood vessel when it impinges on the vessel wall. Thus, it would be desirable if the expander member can be fabricated in such a way that it exhibits a controlled mode of failure, i.e., a rapid rupture so that the pressure is released over a significant area in a short time frame.

SUMMARY OF THE INVENTION

The above-listed desirable characteristics are achieved in accordance with the present invention by forming a multi-layer balloon where the individual layers afford a desirable property to the composite. It has been found that a layer of medium or relatively high melt temperature material which also exhibits high tensile strength with relatively low distensibility can be used to provide the required high burst or tensile strength and low radial expansion at high pressures required by the expander member in a composite structure. This layer may be referred to as the tensile layer or tensile ply. It may be a biaxially-oriented film of relatively high crystallinity.

In the composite structure, the tensile layer is combined as an outer layer with a chemically and physically compatible adhesion or bonding inner layer which is fabricated from materials having superior glue bonding or melt bonding characteristics. The bonding layer also must have good interlayer adhesion characteristics with the material used for the tensile layer. The bonding layer imparts the necessary adhesion properties to properly bond the expander member to the distal end portion of the catheter body. If melt bonding is the desired mode, the material of the bonding layer should have a lower melting point than that of the tensile layer so that melt bonding of the composite may be readily achieved in the fabrication process with minimal effect on the tensile ply. In this regard, it should be noted that the bonding layer may or may not be continuous or coextensive with the entire inner surface of the tensile layer inasmuch as it is required generally only in the vicinity of the expander/catheter interface surfaces.

Examples of materials exhibiting the required high tensile, low distensibility and having medium melt temperatures include certain copolymers such as ABS (acrylonitrile-butadiene-styrene), ABS/nylon, ABS/polyvinyl chloride (PVC) and ABS/polycarbonate. Such materials having high melt temperatures include acrylonitrile copolymer, polyacrylamide, polyacrylate and polyacrylsulfone. Other materials having suitable characteristics include high melt temperature polyesters such as polyethylene terephthalate (PET), polybutylene terephthalate (PBT), polyethylene naphthalate (PEN), liquid crystal polymer (LCP), polyester/polycaprolactone and polyester/polyadipate; and high melt temperature polyethers including polyetheretherketone (PEEK), polyethersulfone (PES), polyetherimide (PEI) and polyetherketone (PEK), polymenthylpentene, polyphenylene ether, polyphenylene sulfide, and styrene acrylonitrile (SAN). It should be noted that LCP has a very high melt temperature and SAN, a lower melt temperature than the other listed polyethers. Additional compounds having the required tensile properties which have a medium melt temperature include polyamides such as nylon 6, nylon 6/6, nylon 6/66, nylon 6/9, nylon 6/10, nylon 6/12, nylon 11 and nylon 12.

Suitable adhesion materials for the bonding layer having a high distensibility but excellent melt bond and glue adhesion properties with relatively low melt temperatures include ethylene, propylene, ethylene vinylacetate and ethylene vinyl alcohol (EVA), various ionomers, polyethylene type I-IV, polyolefins, polyurethane, polyvinyl chloride, and polysiloxanes (silicones). Those with low to medium melt temperatures include fluorocarbons such as polychlorotriethylene (CTFE), poly[ethylene-co-chlorotrifluoroethylene] (ECTFE) copolymer ethylene tetrafluoroethylene (ETFE), copolymer tetrafluoroethylene and hexafluoropropylene (FEP), perfluoroalkane (PFA) and poly[vinylidene fluoride] (PVDF).

It will be appreciated that the particular combination chosen would depend on the particular application and particular catheter involved, and that an array of multilayer expanders of different composition combinations particularly applicable to different situations can be produced. In addition, specific properties required for addressing a specific stenosis could be utilized to produce a tailor-made expander.

More particularly with respect to the process, a tubular parison is first generated in a co-extrusion process whereby different polymeric materials are coaxially layered. Subsequently, the parison is inserted in a blow molding fixture, allowing the tube to be longitudinally drawn and radially expanded until the composite film is oriented, the maximum O.D. of the expander member is defined and a desired film thickness is achieved. For example, in forming the parison, PET of a predetermined viscosity may be coextruded with polyethylene where, forming the parison, the polyethylene lines the lumen thereof. When the expander member is formed from the parison in the blow molding operation, the PET layer affords the desired burst strength and limited radial expansion characteristic while the polyethylene layer enhances the ability to bond the resulting balloon to the catheter body.

The characteristic of lubricity may also be added by coating the exterior of the composite with a suitably lubricious plastic exhibiting high hydrophilic characteristics. Suitable lubricious hydrophilic materials include polycaprolactam polyvinylindol, N-vinylpyrrolidone, various hydrogels, and other hydrophilic lubricious polymeric materials.

One successful embodiment of the system of the invention utilizes a combination of polyethylene terephthalate (PET) as the tensile layer in combination with a bonding layer of polyethylene. The composite PET/polyethylene balloon was coated on the exterior of the PET with polycaprolactam. By forming a three-layer tubular parison having a layer of plastic with known rupture characteristics, the polyethylene layer may provide the bondability attribute, the PET, the limited radial expansion characteristic and/or the controlled rupture characteristic while polycaprolactam again affords the lubricity.

Of course, the known rupture or failure characteristics involve the failure by bursting or large scale rupture of the tensile layer rather than the development of small or pin hole leaks in which a small stream of high pressure fluid is released. This minimizes possible damage to surrounding tissue caused by high pressure fluid leakage from the membrane.

DESCRIPTION OF THE DRAWINGS

The various features, characteristics and advantages of the invention will become apparent to those skilled in the art from the following detailed description of a preferred embodiment, especially when considered in conjunction with the accompanying drawings in which:

FIG. 2 is a partial schematic illustration of apparatus for manufacturing parisons in a co-extrusion process;

FIG. 5 shows the expander joined to the distal end of a catheter; and

FIG. 6 depicts an alternative embodiment of the multilayer expander member.

DESCRIPTION OF THE PREFERRED EMBODIMENT

Figure 1:
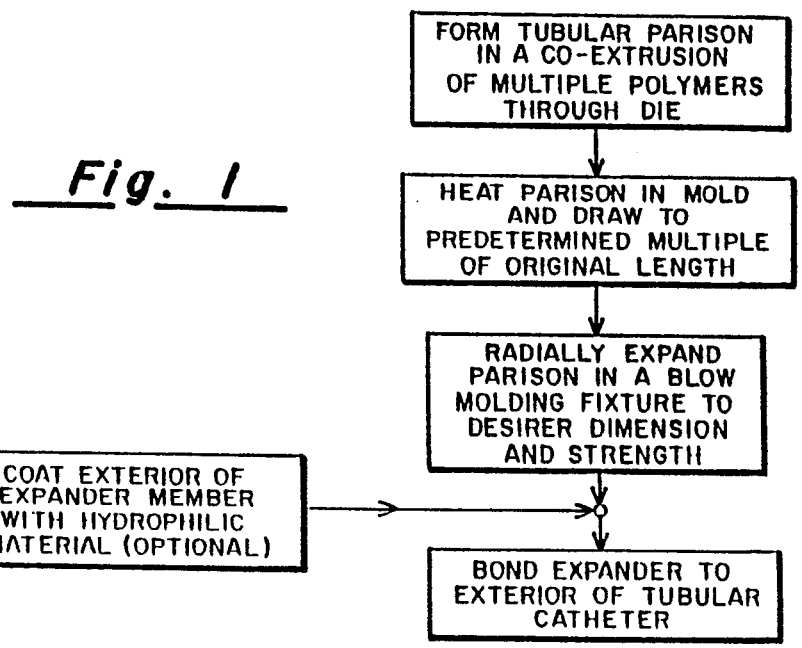
FIG. 1 is a process flow chart illustrative of the present invention.

With reference to FIG. 1, in fabricating the multilayer expander member in accordance with the present invention, the first step in the process is to create a parison which, when heated and then drawn and blown creates a balloon or expander member for use on an intravascular catheter. The extruding apparatus is indicated generally by numeral 10 in FIG. 2 and is seen to comprise a motor 12 coupled in driving relationship to a gear box 14 whose output shaft comprises a coarse-pitched archimedian screw 16 rotating within a heated barrel 18. In accordance with known practice, the screw generally has three distinct sections. In the "feed" section 20, directly beneath the feed hopper 22, the screw channel depth is constant and relatively large and serves to convey solid polymer material from the hopper. The depth of the flute in the "compression" section 24 is uniformly tapered and designed to compact the plastic and force it into contact with the barrel 18 to enhance melting. The melting is achieved mainly by a combination of heat conducted from electrical heating elements 26 contained in the barrel and the heat generated by the intense shearing in the molten layer formed between the barrel and the solid material. Numeral 28 identifies the "metering" section of the screw in which the flute depth is constant and relatively small. It controls the output from the extruder in terms of quantity, steadiness and homogeneity. Disposed at the end of the screw 16 is an extruder die 30 which, in the case of the present invention, provides for co-extrusion of at least two different plastics. The first plastic passing through extruder 10 combines with a second plastic exiting a substantially identical extruder shown schematically at 32 to create a concentrically layered tubular parison, the cross-section of which is seen in the view of FIG. 4.

Figure 3:
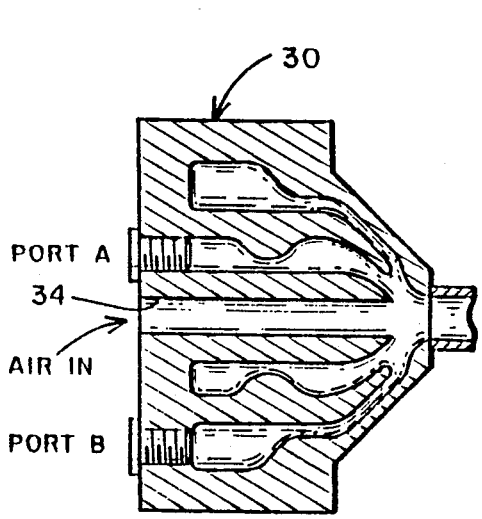
FIG. 3 is a cross-sectional view of a two-component co-extrusion die useful in forming a two-layer parison.

FIG. 3 is a cross-sectional view taken through a two-port co-extrusion die. For example, the output from the metering section 28 of the extruder 10 may be fed into die port A in FIG. 3 while that from the metering section of the screw of extruder 32 feeds port B. The molten plastic flows together to form a layer with the plastic entering port B surrounding the plastic entering port A. As the plastic is made to flow through the die, air is also introduced through the central bore 34 of the die 30 to prevent the collapse of the tubular shaped exudate.

In accordance with one aspect of the invention, the plastic entering port A, for example, may comprise a polyolefin or PVC while that forced into port B may be a homopolyester, preferably PET, of a predetermined viscosity. With these two constituents, the resulting tubular parison will have the PVC as the inner tubular layer and the PET as its outer layer. The thickness of the individual layers will be determined by the mass flow ratios provided by the respective extruders. The final diameter of the parison is determined by the size of the die exit opening, the total flow of material into ports A and B and the take-away or draw speed.

Figure 4:
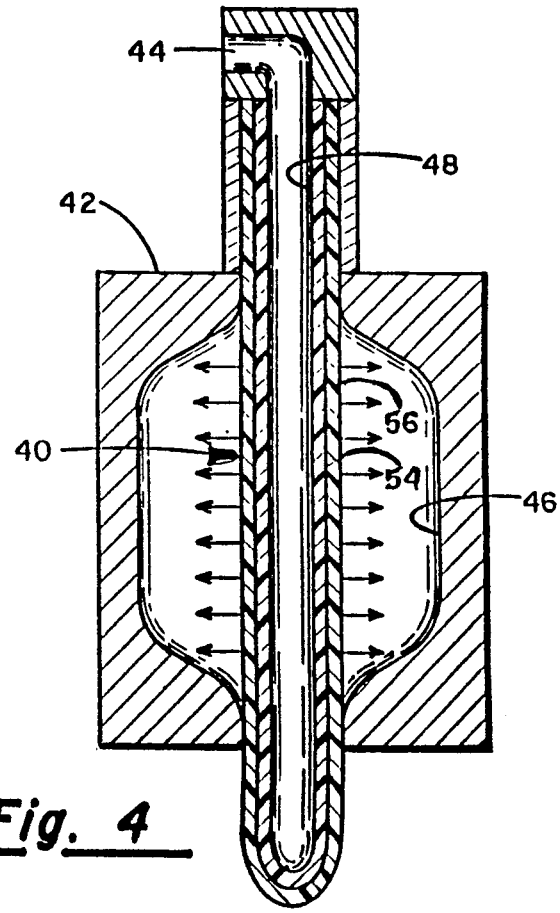
FIG. 4 illustrates schematically an apparatus for blow molding the parison into a biaxially oriented multilayer expander member.

The balloon itself is fabricated in a blow molding operation wherein the parison 40 is inserted into the blow mold 42 as shown in FIG. 4 and air or other suitable fluid is introduced through the port 44 at a predetermined pressure. The mold 42 has a cavity 46 corresponding to the desired size of the balloon to be produced.

After the tubular parison is disposed in the mold, the mold is heated to thereby raise the tubing temperature to a point between the second order transition temperature and the first order transition temperature of the polyester polymer.

Of course, the inner layer can be caused to adhere to and attach the balloon to the exterior of the tubular catheter body in any desired manner. The material of the inner layer may be such that relatively low melt temperature material can be utilized to achieve a permanent melt bond. Preferably, the exterior of the tubular catheter body is provided with a coating of the same or similar material to that of the inner layer of the multilayer balloon structure such that the materials bonded are substantially identical. This also allows the continuous joint to be made utilizing melt bonding the materials. In this regard, it is desired that the material forming the bonding layer of the multilayer system have a melting temperature sufficiently below that of the material of the tensile layer so that the melt bonding can be achieved without affecting the future physical characteristics of the system.

As described above, it is desirable that the expander member itself exhibits rather high tensile strength properties. This means exhibiting a burst pressure well in excess of 7 atmospheres while undergoing a radial expansion less than about 3-10 percent. The actual strength, of course, will depend on the relative tensile strength of the material and thickness of the material layer. In addition, these extruded materials are ones not prone to pinhole leaks in the process of the invention in most cases results in a mode of failure, should failure occur, in the form of a rapid rupture which releases the internal pressure over a considerable area in a short time frame so that damage to the vessel is minimized.

By first drawing the tubular parison and subsequently blow molding same, biaxial orientation takes place whereby the PET layer 56, while remaining flexible, becomes strong as regards the inflation pressure at which the material will burst. When it is desired to bond the finished balloon onto the catheter body as illustrated in FIG. 5, the inner layer 48 of PVC can readily be bonded to an outer PVC tubular body 50 and to an inner tubular body 52, such as by adding adhesive 54 between the outer layer 56 and the inner layer 48. The space between the coaxially disposed tubes allows for injection of a balloon inflation fluid. Balloons produced in accordance with the invention may exhibit a burst pressure well in excess of 7 atmospheres while radially expanding less than about 3-10 percent. While the PVC layer 48 adds little to the burst strength of the composite, it does facilitate the attachment of the balloon to the exterior of the tubular catheter body.

If it is desired to increase the lubricity of the composite balloon, this may be accomplished by dipping or other coating the multilayer balloon in a suitable hydrophilic material such as polyvinylidol, N-vinylpyrolodone, hydrogels, etc.

With reference to FIG. 6 and rather than utilizing PET in combination with PVC, a balloon having enhanced properties maybe created by co-extruding a high molecular weight crystalline polyester 60 with a lower molecular weight amorphous polyester 62 in forming the parison. An outer layer of filled polymer 64 adds lubricity. As known in the art, adhesive 66, 68 may be juxtaposed between layers 60, 62 and 64. Following drawing and radial expansion in a blow molding operation, the resulting balloon is found to exhibit high burst strength, low radial expansion and superior bondability as compared to conventional PET single-layer balloons.

The rupture characteristics of a polymer layer can be modified to increase the rupture rate by adding filler material. The filler materials may be an inert type, such as calcium carbonate, generally in powder form, carbon in fiber form, or an incompatible second phase polymer. Incompatible phase polymer systems afford many advantageous characteristics and are a function of the dispersion between the two phases. Materials which might be candidates for this are polypropylene and selected rubbers, polyester and polypropylene.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A coaxially-layered, multilayer expander member for attachment to a medical catheter body member comprising:
   an outer extruded tensile layer consisting essentially of a biaxially-oriented tubular polymeric film exhibiting high tensile strength and low distensibility;
   an inner bonding layer consisting essentially of a polymeric plastic film co-extruded with the outer tensile layer and adhered to the outer tensile layer, forming therewith a layer combination, the inner bonding layer further being one which adheres readily to a catheter body using a process selected from the group consisting of melt bonding and adhesive bonding; and
   wherein the mode of high pressure failure of the layer combination is for the expander member to rupture rather than develop leaks.

2. A coaxially-layered, multilayer expander member for attachment to a medical catheter body member comprising in combination:
   an outer extruded biaxially-oriented tubular polymeric film tensile layer exhibiting high tensile strength and low distensibility selected from materials of the group consisting of high and medium melt temperature copolymers, high melt temperature polyesters, high melt temperature polyethers, medium melt temperature polyethers, and medium melt temperature polyamides; and
   an inner easily expanded polymeric plastic film bonding layer co-extruded with the outer layer and adhered to the outer tensile layer forming therewith a layer combination the inner bonding layer being one which readily adheres to a catheter body using a process selected from the group consisting of melt bonding and adhesive bonding; and
   wherein the mode of high pressure failure of the layer combination is for the expander member to rupture rather than develop leaks.

3. The multilayer expander member of claim 2 wherein the inner layer is not coextensive with the inner surface of the outer layer.

4. The multilayer expander member of claim 2 wherein:

the outer tensile layer further consists essentially of a material selected from the group consisting of ABS (acrylonitrile-butadiene-styrene), ABS/nylon, ABS/polyvinyl chloride (PVC), ABS/polycarbonate and combinations thereof, acrylonitrile copolymer, polyacrylamide, polyacrylate, polyacrylsulfone, polyethylene terephthalate (PET), polybutylene terephthalate (PBT), polyethylene naphthalate (PEN), liquid crystal polymer (LCP), polyester/polycaprolactone polyester/polyadipate, polyetheretherketone (PEEK), polyethersulfone (PES), polyetherimide (PEI), polyetherketone (PEK), polymenthylpentene, polyphenylene ether, polyphenylene sulfide, styrene acrylonitrile (SAN), nylon 6, nylon 6/6, nylon 6/66, nylon 6/9, nylon 6/10, nylon 6/12, nylon 11 and nylon 12; and wherein the inner bonding layer consists of a material selected from the group consisting of ethylene propylene, ethylene vinylacetate and ethylene vinyl alcohol (EVA), various ionomers, polyethylene type I-IV, polyolefins, polyurethane, polyvinyl chloride, and polysiloxanes (silicones).

5. The multilayer expander member of claim 4 wherein the material of the inner layer adheres to surfaces readily by melt bonding and has a melting point below that of the outer layer.

6. The multilayer expander member of claim 5 wherein the inner layer is not coextensive with the inner surface of the outer layer.

7. The multilayer expander member of claim 2 wherein the material of the inner layer adheres to surfaces readily by melt bonding and has a melting point below that of the outer layer.

8. The multilayer expander as in claim 2 wherein the inner film layer comprises an amorphous polyester.

9. A coaxially-layered, multilayer expander member for attachment to a medical catheter body member comprising:

an outer extruded tensile layer consisting essentially of a biaxially-oriented tubular polymer film exhibiting high tensile strength and low distensibility;

an inner bonding layer consisting essentially of a polymeric plastic film co-extruded with the outer tensile layer and adhered to the outer tensile layer, forming a layer combination, the inner bonding layer further being one which adheres readily to a catheter body using a process selected from the group consisting of melt bonding and adhesive bonding;

wherein the mode of high pressure failure of the layer combination is for the expander member to rupture rather than develop leaks; and a coating of an hydrophilic, lubricous polymer material on the outer surface of the tensile layer.

10. A coaxially-layered, multilayer expander member for attachment to a medical catheter body member comprising in combination:

an outer extruded biaxially-oriented tubular polymeric film tensile layer exhibiting high tensile strength and low distensibility selected from materials of the group consisting of high and medium melt temperature copolymers, high melt temperature polyesters, high melt temperature polyethers, medium melt temperature polyethers, and medium melt temperature polyamides; and an inner easily expanded polymeric plastic film bonding layer co-extruded with the outer layer and adhered to the outer layer the bonding layer being one which readily adheres to a catheter body using a process selected from the group consisting of melt bonding and adhesive bonding;

wherein the mode of high pressure failure of the layer combination is for the expander member to rupture rather than develop leaks; and a coating of an hydrophilic, lubricous polymer material on the outer surface of the tensile layer.

11. The expander as in claim 10 wherein the inner layer comprises a polyolefin.

12. The expander as in claim 10 wherein the hydrophilic polymer is polycaprolactam.

13. A coaxially-layered, multilayer expander member for attachment to a medical catheter body member comprising in combination:

an outer extruded biaxially-oriented tubular polymeric film tensile layer exhibiting high tensile strength and low distensibility selected from materials of the group consisting of ABS (acrylonitrile-butadiene-styrene), ABS/nylon, ABS/polyvinyl chloride (PVC), ABS/polycarbonate and combinations thereof, acrylonitrile copolymer, polyacrylamide, polyacrylate, polyacrylsulfone, polyethylene terephthalate (PET), polybutylene terephthalate (PBT), polyethylene naphthalate (PEN), liquid crystal polymer (LCP), polyester/polycaprolactone polyester/polyadipate, polyetheretherketone (PEEK), polyethersulfone (PES), polyetherimide (PEI), polyetherketone (PEK), polymenthylpentene, polyphenylene ether, polyphenylene sulfide, styrene acrylonitrile (SAN), nylon 6, nylon 6/6, nylon 6/66, nylon 6/9, nylon 6/10, nylon 6/12, nylon 11 and nylon 12;

an inner easily expanded polymeric plastic film bonding layer co-extruded with the outer layer and adhered to the outer tensile layer forming therewith a layer combination the inner bonding layer being one which readily adheres to a catheter body using a process selected from the group consisting of melt bonding and adhesive bonding, wherein the inner bonding layer consists of a material selected from the group consisting of ethylene propylene, ethylene vinylacetate and ethylene vinyl alcohol (EVA), various ionomers, polyethylene type I-IV, polyolefins, polyurethane, polyvinyl chloride, and polysiloxanes (silicones);

a coating of an hydrophilic, lubricous polymer material on the outer surface of the tensile layer; and wherein the mode of high pressure failure of the layer combination is for the expander member to rupture rather than develop leaks.

14. The multilayer expander member of claim 13 wherein the coating of hydrophilic, lubricous polymer material on the outer surface of the tensile layer is selected from the group consisting of polycaprolactam, polyvinylindol and vinyl pyrrolidone and hydrogels.

15. The multilayer expander member of claim 13 wherein the material of the inner layer adheres to surfaces readily by melt bonding and has a melting point below that of the outer layer.

16. The multilayer expander member of claim 14 wherein the material of the inner layer adheres to surfaces readily by melt bonding and has a melting point below that of the outer layer.

17. An expander member for attachment to an intravascular catheter body member comprising:

an outer coating layer of an hydrophilic, lubricous polymer;

an extruded tubular tensile layer of biaxially oriented polyethylene terephthalate carrying the outer coating layer and exhibiting a radial expansion not exceeding 3-10 percent;

an inner tubular layer of an amorphous polyester plastic material co-extruded with the tensile layer coaxially adhered to the tensile layer;

wherein the predetermined burst pressure is in excess of 7 atmospheres pressure; and wherein the expander member has failure characteristics in which the expander will burst rather than develop small leaks.

18. The expander as in claim 17 and further including hot-melt adhesive layers disposed between the tensile and inner layers.

* * * * *